United States Patent
Eidenschink

(10) Patent No.: US 8,231,647 B2
(45) Date of Patent: *Jul. 31, 2012

(54) CATHETER HAVING AN IMPROVED TORQUE TRANSMITTING SHAFT

(75) Inventor: Tracee E. J. Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 368 days.

This patent is subject to a terminal disclaimer.

(21) Appl. No.: 12/347,670

(22) Filed: Dec. 31, 2008

(65) Prior Publication Data

US 2009/0118759 A1    May 7, 2009

Related U.S. Application Data

(63) Continuation of application No. 10/034,586, filed on Dec. 27, 2001, now Pat. No. 7,488,338.

(51) Int. Cl.
*A61M 29/00* (2006.01)
(52) U.S. Cl. .................... 606/194; 604/103
(58) Field of Classification Search ............... 606/108, 606/159, 194, 195, 192, 198; 623/1.11; 604/96.01, 604/103, 524; 600/433, 435
See application file for complete search history.

(56) References Cited

U.S. PATENT DOCUMENTS

| | | |
|---|---|---|
| 3,467,101 A | 9/1969 | Fogarty et al. |
| 3,612,058 A | 10/1971 | Ackerman |
| 3,878,849 A | 4/1975 | Muller et al. |
| 4,385,635 A | 5/1983 | Ruiz |
| 4,425,919 A | 1/1984 | Alston, Jr. et al. |
| 4,430,083 A | 2/1984 | Ganz et al. |
| 4,465,482 A | 8/1984 | Tittel |
| 4,547,193 A | 10/1985 | Rydell |
| 4,569,347 A | 2/1986 | Frisbie |
| 4,669,465 A | 6/1987 | Moore et al. |
| 4,690,175 A | 9/1987 | Ouchi et al. |
| 4,801,297 A | 1/1989 | Mueller |
| 4,817,613 A | 4/1989 | Jaraczewski et al. |
| 4,842,590 A | 6/1989 | Tanabe et al. |
| 4,925,445 A | 5/1990 | Sakamoto et al. |
| 4,960,410 A | 10/1990 | Pinchuk |
| 4,998,923 A | 3/1991 | Samson et al. |
| 5,001,825 A | 3/1991 | Halpern |
| 5,047,045 A | 9/1991 | Arney et al. |

(Continued)

FOREIGN PATENT DOCUMENTS

DE    41 04 092 A1    8/1991

(Continued)

OTHER PUBLICATIONS

U.S. Appl. No. 09/430,327 to Centell et al., filed Oct. 29, 1999.

*Primary Examiner* — Victor Nguyen
(74) *Attorney, Agent, or Firm* — Seager, Tufte & Wickhem, LLC

(57) ABSTRACT

The present invention relates generally to a catheter having a torque transmitting shaft which retains adequate flexibility. The catheter includes an elongate shaft having an outer surface. In a preferred embodiment, a raised pattern is disposed on the outer surface. Preferably, the raised pattern improves the transmission of torque along the elongate shaft by including a series of bearing points which contact other bearing points along the shaft when torqued.

11 Claims, 1 Drawing Sheet

U.S. PATENT DOCUMENTS

| | | |
|---|---|---|
| 5,069,226 A | 12/1991 | Yamauchi et al. |
| 5,095,915 A | 3/1992 | Engelson |
| 5,100,381 A | 3/1992 | Burns |
| 5,114,402 A | 5/1992 | McCoy |
| 5,156,594 A | 10/1992 | Keith |
| 5,180,376 A | 1/1993 | Fischell |
| 5,213,111 A | 5/1993 | Cook et al. |
| 5,318,526 A | 6/1994 | Cohen |
| 5,329,923 A | 7/1994 | Lundquist |
| 5,358,493 A | 10/1994 | Schwiech, Jr. et al. |
| 5,364,357 A | 11/1994 | Aase |
| 5,381,782 A | 1/1995 | DeLaRama et al. |
| 5,409,015 A | 4/1995 | Palermo |
| 5,437,288 A | 8/1995 | Schwartz et al. |
| 5,443,455 A | 8/1995 | Hergenrother et al. |
| 5,449,343 A | 9/1995 | Samson et al. |
| 5,452,726 A | 9/1995 | Burmeister et al. |
| 5,454,787 A | 10/1995 | Lundquist |
| 5,456,665 A | 10/1995 | Postell et al. |
| 5,458,605 A | 10/1995 | Klemm |
| 5,507,766 A | 4/1996 | Kugo et al. |
| 5,531,719 A | 7/1996 | Takahashi |
| 5,542,434 A | 8/1996 | Imran et al. |
| 5,546,958 A | 8/1996 | Thorud et al. |
| 5,549,551 A | 8/1996 | Peacock, III et al. |
| 5,549,552 A | 8/1996 | Peters et al. |
| 5,569,200 A | 10/1996 | Umeno et al. |
| 5,571,114 A | 11/1996 | Devanaboyina |
| 5,573,520 A | 11/1996 | Schwartz et al. |
| 5,596,996 A | 1/1997 | Johanson et al. |
| 5,605,543 A | 2/1997 | Swanson |
| 5,636,642 A | 6/1997 | Palermo |
| 5,700,253 A | 12/1997 | Parker |
| 5,716,410 A | 2/1998 | Wang et al. |
| 5,720,724 A | 2/1998 | Ressemann et al. |
| 5,722,424 A | 3/1998 | Engelson |
| 5,741,429 A | 4/1998 | Donadio, III et al. |
| 5,743,876 A | 4/1998 | Swanson |
| 5,749,837 A | 5/1998 | Palermo |
| 5,750,206 A | 5/1998 | Hergenrother et al. |
| 5,766,164 A | 6/1998 | Mueller et al. |
| 5,769,796 A | 6/1998 | Palermo et al. |
| 5,772,609 A | 6/1998 | Nguyen et al. |
| 5,776,100 A | 7/1998 | Forman |
| 5,780,807 A | 7/1998 | Saunders |
| 5,782,809 A | 7/1998 | Umeno et al. |
| 5,813,997 A | 9/1998 | Imran et al. |
| 5,814,063 A | 9/1998 | Freitag |
| 5,827,201 A | 10/1998 | Samson et al. |
| 5,833,632 A | 11/1998 | Jacobsen et al. |
| 5,836,893 A | 11/1998 | Urick |
| 5,843,031 A | 12/1998 | Hermann et al. |
| 5,843,050 A | 12/1998 | Jones et al. |
| 5,855,560 A | 1/1999 | Idaomi et al. |
| 5,860,938 A | 1/1999 | Lafontaine et al. |
| 5,916,177 A | 6/1999 | Schwager |
| 5,916,178 A | 6/1999 | Noon et al. |
| 5,921,956 A | 7/1999 | Grinberg et al. |
| 5,921,958 A | 7/1999 | Ressemann et al. |
| 5,938,623 A | 8/1999 | Quiachon et al. |
| 5,951,539 A | 9/1999 | Nita et al. |
| 5,964,714 A | 10/1999 | Lafontaine |
| 5,984,878 A | 11/1999 | Engelson |
| 6,001,068 A | 12/1999 | Uchino et al. |
| 6,004,279 A | 12/1999 | Crowley et al. |
| 6,017,319 A | 1/2000 | Jacobsen et al. |
| 6,019,736 A | 2/2000 | Avellanet et al. |
| 6,024,764 A | 2/2000 | Schroeppel |
| 6,027,863 A | 2/2000 | Donadio, III |
| 6,036,670 A | 3/2000 | Wijeratne et al. |
| 6,048,338 A | 4/2000 | Larson et al. |
| 6,090,072 A | 7/2000 | Kratoska et al. |
| 6,096,012 A | 8/2000 | Bogert et al. |
| 6,102,890 A | 8/2000 | Stivland et al. |
| 6,139,510 A | 10/2000 | Palermo |
| 6,146,339 A | 11/2000 | Biagtan et al. |
| 6,160,084 A | 12/2000 | Langer et al. |
| 6,165,163 A | 12/2000 | Chien et al. |
| 6,168,604 B1 | 1/2001 | Cano |
| 6,183,443 B1 | 2/2001 | Kratoska et al. |
| 6,193,706 B1 | 2/2001 | Thorud et al. |
| 6,258,099 B1 * | 7/2001 | Mareiro et al. ............... 606/108 |
| 6,273,879 B1 | 8/2001 | Keith et al. |
| 6,368,316 B1 | 4/2002 | Jansen et al. |
| 6,569,192 B1 * | 5/2003 | Foreman et al. ............. 623/1.11 |
| 6,574,497 B1 | 6/2003 | Pacetti |
| 6,602,225 B2 | 8/2003 | Eidenschink et al. |
| 6,607,505 B1 | 8/2003 | Thompson et al. |
| 7,488,338 B2 * | 2/2009 | Eidenschink ................. 606/194 |
| 2001/0037085 A1 | 11/2001 | Keith et al. |

FOREIGN PATENT DOCUMENTS

| | | |
|---|---|---|
| EP | 0 063 859 A2 | 11/1982 |
| EP | 0 102 685 A2 | 3/1984 |
| EP | 0 370 785 A1 | 5/1990 |
| EP | 0 411 118 A1 | 2/1991 |
| EP | 0 437 795 A1 | 7/1991 |
| EP | 0 594 201 A2 | 4/1994 |
| EP | 0 608 853 A2 | 8/1994 |
| EP | 0 631 791 B1 | 1/1995 |
| EP | 0 688 576 A1 | 12/1995 |
| EP | 0 778 039 A1 | 6/1997 |
| EP | 0 806 220 B1 | 11/1997 |
| FR | 2 713 492 A1 | 6/1995 |
| JP | 8-257128 A | 10/1996 |
| JP | 10-118188 | 5/1998 |
| JP | 2000-254235 A | 9/2000 |
| WO | 93/04722 A2 | 3/1993 |
| WO | 96/38193 A1 | 12/1996 |
| WO | 99/11313 A1 | 3/1999 |

* cited by examiner

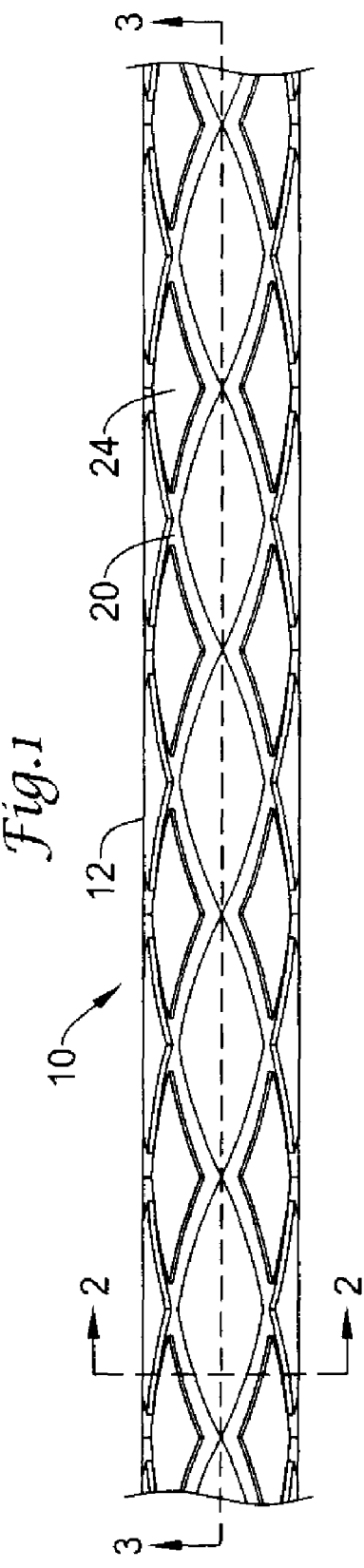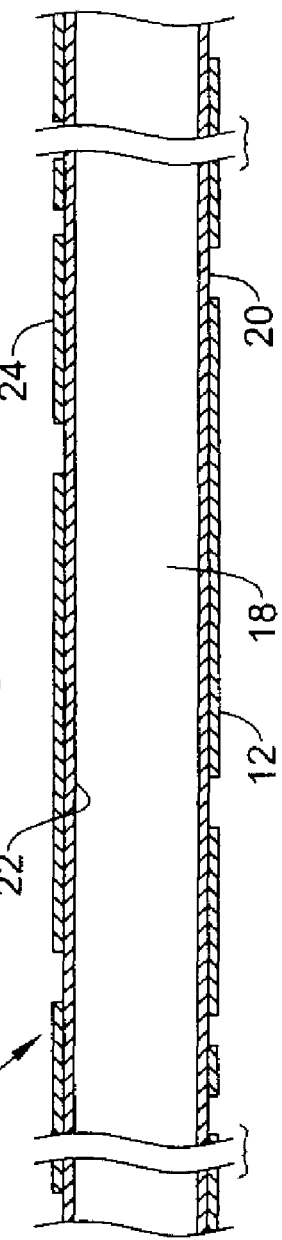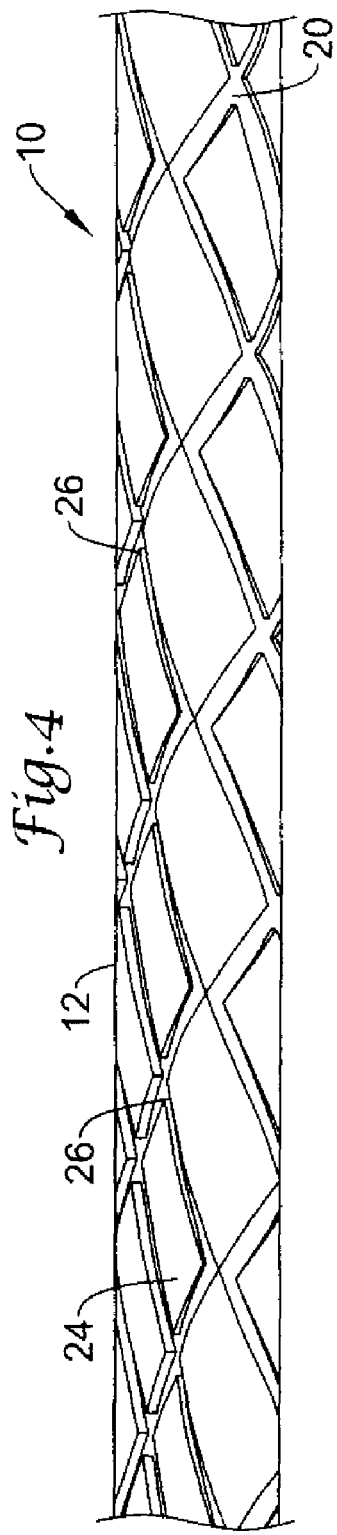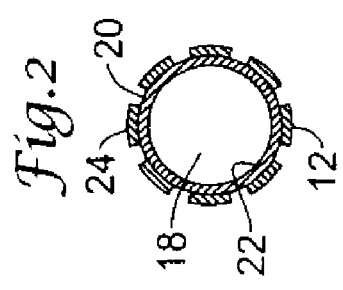

CATHETER HAVING AN IMPROVED TORQUE TRANSMITTING SHAFT

CROSS REFERENCE TO RELATED APPLICATIONS

This application is a continuation of U.S. application Ser. No. 10/034,586, filed Dec. 27, 2001, now U.S. Pat. No. 7,488,338, the entire disclosure of which is incorporated herein by reference.

FIELD OF THE INVENTION

The present invention relates generally to catheters for performing medical procedures including intravascular procedures such as percutaneous transluminal coronary angioplasty. More particularly, the present invention relates to catheters with an improved shaft design.

BACKGROUND OF THE INVENTION

The use of intravascular catheters has become an effective method for treating many types of vascular disease. In general an intravascular catheter is inserted into the vascular system of the patient and navigated through the vasculature to a desired target site. Using this method, virtually any target site in the patient's vascular system may be accessed, including the coronary, cerebral, and peripheral vasculature. Examples of therapeutic purposes for intravascular catheters include percutaneous transluminal angioplasty (PTA) and percutaneous transluminal coronary angioplasty (PTCA).

Catheters are also known for use in other body lumens for non-vascular therapeutic purposes. These can include pancreato-biliary treatments and urological applications.

Generally, a catheter enables a physician to remotely perform a medical procedure by inserting the catheter into a body lumen, such as a blood vessel, of a patient at a location that is easily accessible, and thereafter navigating the catheter to the desired target site. By this method, virtually any target site, whether in the patient's vascular or non-vascular lumen, may be remotely accessed. In vascular applications, the catheter typically enters the patient's vasculature at a convenient location such as a blood vessel in the arm, neck or near the groin. In both vascular and non-vascular applications, the path taken by the catheter through the body lumen is generally tortuous, requiring the catheter to change direction frequently. It may also be necessary for the catheter to double back on itself. Physicians often apply torsional forces to the proximal portion of the catheter to aid in steering the catheter. To facilitate the steering process, it is desirable that an intravascular catheter have a relatively high level of torqueability. Furthermore, in order for the catheter to conform to a patient's tortuous anatomy, it is desirable that the catheter be relatively flexible. The requirement that the catheter include a relatively high level of torqueability and yet remain flexible is at times a competing requirement, as increasing wall thickness of a catheter shaft tends to increase torqueability while compromising flexibility.

Guide catheters are one type of catheter used in both vascular and non-vascular procedures to aid in delivering other catheters or other interventional medical devices to a treatment site in a vessel or other lumen within the body. In a routine coronary angioplasty procedure, a guiding catheter is introduced into a peripheral artery and advanced over a guidewire through the aorta until the distal end of the guide catheter is engaged with the appropriate coronary ostium. Next, a balloon dilatation catheter is introduced over the guidewire and through the guide catheter. The guidewire is advanced past the distal end of the catheter within the lumen of the diseased vessel and manipulated across the region of the stenosis. The balloon dilatation catheter is then advanced past the distal end of the guide catheter over the guidewire until the balloon is positioned across the treatment site. After the balloon is inflated to dilate the blood vessel in the region of the treatment site, the guidewire, balloon dilatation catheter and guide catheter can be withdrawn.

Likewise, angiographic catheters can be used in evaluating the progress of coronary artery disease in patients. Angiography procedures are used to view the patency of selected blood vessels. In carrying out this procedure, a diagnostic catheter having a desired distal end curvature may be advanced over a guidewire through the vascular system of the patient until the distal end of the catheter is steered into the particular coronary artery to be examined. Diagnostic catheters are also used in non-vascular procedures to assess disease state.

Balloon catheters used with the above-described guide catheters are typically classified as over-the-wire (OTW) or single operator exchange (SOE). An OTW catheter includes a guidewire lumen extending through a tubular shaft from the distal tip of the catheter to the proximal end of the catheter. A second tubular shaft extends coaxially over the first shaft to form an annular inflation lumen therebetween in fluid communication with a balloon disposed near the distal end of the two shafts.

SOE catheters have a relatively short guidewire lumen relative to the length of the catheter which extends through a first tubular shaft. The first tubular shaft is usually disposed within a lumen of a second tubular shaft which extends the length of the catheter. The second tubular shaft lumen again provides means for inflating the balloon disposed near the distal end of the shaft assembly.

A common feature to all catheters is the need for shaft assemblies which have adequate torque transmission and yet retain sufficient flexibility to reach desired treatment sites. Tubular members having lumens therethrough are generally used to form the shaft assemblies and selection and design of the tubular members determines the resulting balance between torqueability and flexibility.

SUMMARY OF THE INVENTION

The present invention relates generally to catheters for performing medical procedures including percutaneous transluminal coronary angioplasty. More particularly, the present invention relates to catheters with an improved shaft design. Preferably, the present invention comprises a catheter with an improved torque transmitting shaft. In an exemplary embodiment, the current invention comprises a catheter having an improved torque transmitting shaft and having a desired amount of flexibility.

In a preferred embodiment, a catheter comprises an elongate shaft having a proximal end and a distal end. Preferably, a lumen extends between the proximal end and the distal end. In a preferred embodiment, the elongate shaft further comprises an outer surface and an inner surface. In an exemplary embodiment, the inner surface defines and is in fluid communication with the lumen.

In a preferred embodiment, a raised pattern is disposed at the outer surface. The raised pattern may include a number of shapes and patterns. According to a preferred embodiment of the present invention, a pattern is understood to include regular, irregular, and random arrangements of a design or object. For example, the raised pattern may resemble a tire tread pattern, a plurality of castellations, a diamond-shaped tread pattern, an embossed pattern, etc.

In a preferred embodiment, the catheter may include, but is not limited to, a single-operator-exchange catheter, an over-the-wire catheter, a guide catheter, a balloon catheter, an angioplasty catheter, an atherectomy catheter, etc. Moreover, the elongate shaft may comprise one or more components of a catheter. According to the current invention, the elongate shaft may include an inner shaft, an outer shaft, or both.

According to multiple embodiments of the current invention, the raised pattern can be formed on the outer surface by a number of methods including, but not limited to, laser ablation, overmolding, hot die casting, embossing, and extrusion. In a preferred embodiment, the raised pattern can be formed by removing a portion of the outer surface. For example, a portion of the outer surface can be removed by laser ablation. In one preferred embodiment, when a portion of the outer surface is removed, for example by laser ablation, no more than about 25%-75% of the wall thickness on the outer surface is removed. Preferably no more than about 65%-75% of the wall thickness of the outer surface is removed. In an alternative embodiment, the raised pattern can be formed by embedding a braid into the outer surface, preferably when the polymer shaft is heated or softened, then cooled. The braid is then removed, and the pattern left by the braid forms the raised pattern.

In a preferred embodiment, the thickness of the outer surface is somewhat greater than what is typically used in the art. For example, the thickness of typical outer surfaces may be about 0.001 inches to 0.01 inches. In a preferred embodiment of the current invention, the outer surface may have a thickness of about 0.002 inches. According to a preferred embodiment, forming the raised pattern, for example by laser ablation, may eliminate about 65%-70% of the wall thickness on the outer surface. According to this embodiment, the outer surface substantially emulates the thickness of thin-walled tubing. Preferably, emulation of thin-walled tubing provides the elongate shaft with the desired level of flexibility.

In a preferred embodiment, the raised pattern improves the transmission of torque along the elongate shaft. In a preferred embodiment of the current invention, the raised pattern can provide a high degree of torque transmittance while maintaining a high degree of flexibility. According to a preferred embodiment of the current invention, torque transmission is understood to mean that applying torque to one end of an object, for example, the proximal end of the elongate shaft, results in a substantially equivalent amount of torque at another end of the object, for example, the distal end of the elongate shaft.

In a preferred embodiment, when the elongate shaft is torqued, the raised pattern comes in contact with itself, creating a plurality of bearing points. According to a preferred embodiment, the bearing points are understood to be contact points within or between portions of the raised pattern that contact one another when the elongate shaft is torqued. Preferably, the bearing points transmit torque. In an exemplary embodiment, the bearing points will prevent the failure of torque transmission along the elongate shaft.

BRIEF DESCRIPTION OF THE DRAWINGS

FIG. 1 is a plan view of a portion of a catheter shaft according to a preferred embodiment of the invention;

FIG. 2 is a cross-sectional view of the catheter shaft through line 2-2 of FIG. 1 according to a preferred embodiment of the invention;

FIG. 3 is a cross-sectional view of the catheter through line 3-3 of FIG. 1 according to a preferred embodiment of the invention; and FIG. 4 is a plan view of the catheter shaft of FIG. 1 depicting transmission of torque according to a preferred embodiment of the invention.

DETAILED DESCRIPTION OF THE PREFERRED EMBODIMENTS

Referring now to the drawings wherein like reference numerals indicate like elements throughout the several views, FIG. 1 is a plan view of a portion of a catheter according to a preferred embodiment of the invention. In a preferred embodiment, a catheter 10 comprises an elongate shaft 12. Preferably, elongate shaft 12 further comprises a proximal end (not shown) and a distal end (not shown).

In a preferred embodiment, catheter 10 may include, but is not limited to, a single-operator-exchange catheter, an over-the-wire catheter, a guide catheter, a balloon catheter, an angioplasty catheter, an atherectomy catheter, etc. A person of ordinary skill in the art would be familiar with different types of catheters appropriate for multiple embodiments of the present invention.

In a preferred embodiment, elongate shaft 12 may comprise one or more components of catheter 10. For example, catheter 10 may further comprise an inner shaft, an outer shaft, or both. According to this embodiment, elongate shaft 12 may comprise the inner shaft, outer shaft, or both.

According to a preferred embodiment, elongate shaft 12 can be manufactured from a number of materials including, but not limited to, stainless steel metal, nickel alloy, nickel-titanium alloy, hollow cylindrical stock, thermoplastics, high performance engineering resins, polymer, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, or perfluoro(propyl vinyl ether) (PFA). Preferably, elongate shaft 12 is manufactured so as to maintain the desired level of flexibility and torqueability according to multiple embodiments of the current invention.

In a preferred embodiment, elongate shaft 12 further comprises an outer surface 20. Preferably, outer surface 20 comprises materials similar to those disclosed above including metals and polymers. In an exemplary embodiment, outer surface 20 comprises a unique surface disposed on elongate shaft 12. For example, outer surface 20 may comprise a polymer sheath disposed over elongate shaft 12.

In a preferred embodiment, a raised pattern 24 is disposed at outer surface 20. Raised pattern 24 may include a number of shapes and patterns. According to a preferred embodiment of the present invention, a pattern is understood to include regular, irregular, and random arrangements of a design or objects. For example, raised pattern 24 may resemble a tire tread pattern, a plurality of castellations, a diamond-shaped tread pattern, an embossed pattern, a plurality of turrets, etc.

According to multiple embodiments of the current invention, raised pattern 24 can be formed on outer surface 20 by a number of methods including, but not limited to, laser ablation, overmolding, hot die casting, embossing, and extrusion. In a preferred embodiment, raised pattern 24 can be formed by removing a portion of outer surface 20. For example, a portion of outer surface 20 can be removed by laser ablation. In one embodiment, when a portion of outer surface 20 is removed, for example by laser ablation, no more than about 25%-75% of the wall thickness on the outer surface 20 is removed. Preferably about 60%-75% of the wall thickness on the outer surface is removed. In an alternative embodiment, the raised pattern can be formed by embedding a braid into the outer surface, preferably when the polymer shaft is heated and softened, then cooled with the braid in place. Upon removal of the braid, the raised pattern is left.

In a preferred embodiment, the thickness of the shaft wall is somewhat greater than what is typically used in the art. For example, the thickness of typical shaft walls may be about 0.001 inches to 0.001 inches. In a preferred embodiment, the shaft wall may have a thickness of about 0.002 inches. According to a preferred embodiment, forming raised pattern 24, for example by laser ablation, may eliminate about 60%-70% of the wall thickness of the shaft wall. According to this embodiment, outer surface 20 substantially emulates the thickness of thin-walled tubing. Preferably, emulation of thin-walled tubing provides elongate shaft 12 with the desired level of flexibility.

Because the path taken by a catheter through the vascular system is tortuous, it can be advantageous for a catheter, for example catheter 10 comprising elongate shaft 12, to be highly flexible. Preferably, elongate shaft 12 is flexible. In an exemplary embodiment, elongate shaft 12 emulates the flexibility of thin-walled tubing. According to this embodiment, elongate shaft 12 comprises an amount of flexibility suitable for performing an appropriate medical procedure.

In a preferred embodiment, raised pattern 24 improves the transmission of torque along elongate shaft 12. In an exemplary embodiment of the current invention, raised pattern 24 can provide a high degree of torque transmittance while maintaining a high degree of flexibility. For example, catheter 10 may comprise an elongate shaft with the desired amount of flexibility and improved torque transmission. According to a preferred embodiment of the current invention, torque transmission is understood to mean that applying torque to one end of an object, for example the proximal end of elongate shaft 12, results in a substantially equivalent amount of torque at another end of the object, for example distal end of elongate shaft 12.

In a preferred embodiment, elongate shaft 12 includes means for improving torqueability. Torsional forces applied at the proximal end preferably translate to the distal end to aid in steering. Because of the tortuous path of the vascular system, the combination of flexibility and torqueability may aid in steering a catheter, for example catheter 10.

FIG. 2 is a cross-sectional view of the catheter shaft through line 2-2 of FIG. 1. According to a preferred embodiment, catheter 10 comprises elongate shaft 12 having lumen 18, outer surface 20, and inner surface 22.

In a preferred embodiment, a raised pattern 24 is disposed at outer surface 20. Similar to what is disclosed above, raised pattern 24 may include a number of shapes and patterns and can be formed on outer surface 20 by a number of methods. As indicated, in a non-torqued state, the raised patterns maintain space between them which makes the untorqued shaft more flexible than a smooth-surfaced shaft of equal diameter and overall wall thickness.

In a preferred embodiment, when elongate shaft 12 is torqued, surfaces or portions of raised pattern 24 come in contact with other portions or surfaces of raised pattern 24, creating a plurality of bearing points (not shown, please see element 26 of FIG. 4). The bearing points transmit torque. In an exemplary embodiment, raised pattern 24 improves torque transmission with minimal negative effects on the flexibility of elongate shaft 12 when not torqued.

FIG. 3 is a cross-sectional view of the catheter shaft portion through line 3-3 of FIG. 1 according to a preferred embodiment of the invention. According to a preferred embodiment, catheter 10 comprises elongate shaft 12 having a proximal end (not shown) and a distal end (not shown). Preferably, elongate shaft 12 further comprises outer surface 20. In an exemplary embodiment, a lumen IS extends between the proximal end and the distal end.

In an exemplary embodiment, elongate shaft 12 further comprises an inner surface 22. In a preferred embodiment, inner surface 22 is in fluid communication with lumen 18. Preferably, alternate embodiments of elongate shaft 12, for example elongate shaft 12 including inner surface 22, are appropriate for alternative catheters 10 such as single-operator-exchange catheters, over-the-wire catheters, guide catheters, balloon catheters, angioplasty catheters, atherectomy catheters, etc.

In a preferred embodiment, the raised pattern 24 is disposed at outer surface 20. Similar to what is disclosed above, raised pattern 24 may include a number of shapes and patterns and can be formed on outer surface 20 by a number of methods. As indicated in this view, flexibility is maintained by the spacing between elements of the raised pattern 24.

The raised pattern 24 improves the transmission of torque along elongate shaft 12. When elongate shaft 12 is torqued, raised pattern 24 comes in contact with itself creating a plurality of bearing points (not shown, please see element 26 of FIG. 4). Preferably, the bearing points transmit torque along elongate shaft 12. In a preferred embodiment, the transmission of torque along elongate shaft 12 is understood to be the transmission of torque longitudinally along elongate shaft 12.

FIG. 4 is a plan view of the catheter shaft portion of FIG. 1 transmitting torque according to a preferred embodiment of the invention. According to a preferred embodiment, catheter 10 comprises elongate shaft 12 having a proximal end and a distal end. Preferably, elongate shaft 12 further comprises outer surface 20.

In a preferred embodiment, a raised pattern 24 is disposed at outer surface 20. Raised pattern 24 may include a number of shapes and patterns and can be formed on outer surface 20 by a number of methods.

In a preferred embodiment, when elongate shaft 12 is torqued, raised pattern 24 comes in contact with itself creating a plurality of bearing points 26 providing a means for torque transmission. According to a preferred embodiment, bearing points 26 are understood to be contact points within or between portions of raised pattern 24 over at least a portion of the catheter shaft length that contact one another when elongate shaft 12 is torqued. Preferably, bearing points 26 transmit torque along elongate shaft 12. In a preferred embodiment, the transmission of torque along elongate shaft 12 is understood to be the transmission of torque longitudinally along at least a portion of elongate shaft 12.

In an exemplary embodiment, raised pattern 24 improves torque transmission with minimal negative effects on the flexibility of elongate shaft 12. For example, catheter 10 may comprise an elongate shaft with the desired amount of flexibility and improved torque transmission. In an exemplary embodiment, bearing points 26 will prevent the failure of torque transmission along elongate shaft 12. According to a preferred embodiment, torque transmission is understood to mean that applying torque to one end of an object, for example the proximal end of elongate shaft 12, results in a substantially equivalent amount of torque at another end of the object, for example the distal end of elongate shaft 12.

In use, catheter 10 may be used to perform an appropriate medical procedure. According to a preferred embodiment, the medical procedure may include, but is not limited to, catheterization, angioplasty, atherectomy, diagnosis, etc. When performing the medical procedure, catheter 10 may be inserted into the vasculature or other body lumen of a patient and guided to a target region. In a preferred embodiment, raised pattern 24 on elongate shaft 12 will impart a desired amount of flexibility and torqueability. Preferably, the desired flexibility and torqueability will aid in steering catheter 10 to a target region.

In a preferred embodiment, when catheter 10 is torqued, bearing points 26 within raised pattern 24 will contact one another. Preferably, when catheter 10 is torqued, bearing points 26 will transfer torque along elongate shaft 12.

Numerous advantages of the invention covered by this document have been set forth in the foregoing description. It will be understood, however, that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device having a torque transmitting shaft, comprising:
    an elongate shaft having a proximal end, a distal end, and an outer surface; and
    a raised pattern of generally noncontiguous elements disposed on the outer surface of the elongate shaft wherein the raised pattern improves the transmission of torque along the elongate shaft;
    wherein the raised pattern further comprises a plurality of bearing points;
    wherein the bearing points are separated when the shaft is not being torqued;
    wherein at least two of the bearing points move toward one another when the shaft is torqued.

2. The medical device of claim 1, wherein the bearing points contact one another when the elongate shaft is under torsion.

3. The medical device of claim 1, wherein the raised pattern is formed by laser ablation.

4. The medical device of claim 1, wherein the raised pattern is formed by overmolding.

5. The medical device of claim 1, wherein the raised pattern is formed by hot die casting.

6. The medical device of claim 1, wherein the raised pattern is formed by embossing.

7. The medical device of claim 1, wherein the raised pattern is formed by extrusion.

8. A medical device having a torque transmitting shaft, comprising:
    an elongate shaft having wall defining an inner surface and an outer surface; and
    a plurality of raised elements extending from the outer surface of the elongate shaft, wherein the plurality of raised elements define means for improving the transmission of torque along the elongate shaft when torqued;
    wherein adjacent raised elements are separated when the shaft is not under torsion and wherein at least two adjacent raised elements deflect toward one another when the shaft is under torsion.

9. The medical device of claim 8, wherein the plurality of raised elements are integral with the outer surface of the elongate shaft.

10. The medical device of claim 9, wherein the raised elements are formed by removing a portion of the outer surface.

11. The medical device of claim 8, wherein the raised elements are generally noncontiguous with one another.

\* \* \* \* \*

UNITED STATES PATENT AND TRADEMARK OFFICE
CERTIFICATE OF CORRECTION

PATENT NO. : 8,231,647 B2  Page 1 of 1
APPLICATION NO. : 12/347670
DATED : July 31, 2012
INVENTOR(S) : Tracee E. J. Eidenschink It is certified that error appears in the above-identified patent and that said Letters Patent is hereby corrected as shown below:

Column 6
Line 5: delete "IS" and insert therefor -- 18 --.

Signed and Sealed this
Fifteenth Day of January, 2013

David J. Kappos
*Director of the United States Patent and Trademark Office*